(12) United States Patent
Cottard et al.

(10) Patent No.: US 7,066,966 B2
(45) Date of Patent: *Jun. 27, 2006

(54) OXIDATION DYEING COMPOSITION FOR KERATIN FIBERS COMPRISING A CATIONIC POLY(VINYLLACTAM)

(75) Inventors: François Cottard, Levallois-Perret (FR); Roland De La Mettrie, Le Vésinet (FR)

(73) Assignee: L'oreal S.A., Paris (FR)

( * ) Notice: Subject to any disclaimer, the term of this patent is extended or adjusted under 35 U.S.C. 154(b) by 44 days.

This patent is subject to a terminal disclaimer.

(21) Appl. No.: 10/470,131

(22) PCT Filed: Jan. 22, 2002

(86) PCT No.: PCT/FR02/00253

§ 371 (c)(1),
(2), (4) Date: Mar. 26, 2004

(87) PCT Pub. No.: WO02/058647

PCT Pub. Date: Aug. 1, 2002

(65) Prior Publication Data

US 2004/0205901 A1    Oct. 21, 2004

(30) Foreign Application Priority Data

Jan. 26, 2001  (FR) .................................. 01 01106

(51) Int. Cl.
*A61K 7/13*     (2006.01)
(52) U.S. Cl. ...................... 8/405; 8/406; 8/410; 8/411; 8/421; 8/554; 8/606
(58) Field of Classification Search ................... 8/405, 8/406, 410, 411, 421, 554, 606
See application file for complete search history.

(56) References Cited

U.S. PATENT DOCUMENTS

| | | | |
|---|---|---|---|
| 5,143,518 A | 9/1992 | Madrange et al. | 8/405 |
| 6,207,778 B1 | 3/2001 | Jachowicz et al. | 526/258 |
| 6,602,303 B1* | 8/2003 | Laurent et al. | 8/405 |
| 2002/0046431 A1* | 4/2002 | Laurent et al. | 8/405 |
| 2003/0192134 A1 | 10/2003 | Desenne et al. | 8/405 |
| 2004/0115156 A1 | 6/2004 | De La Mettrie | 424/70.15 |
| 2004/0205901 A1 | 10/2004 | Cottard et al. | 8/405 |

FOREIGN PATENT DOCUMENTS

| | | |
|---|---|---|
| EP | 1 179 336 | 2/2002 |
| EP | 1 321 134 | 6/2003 |
| FR | 2 820 032 | 8/2002 |
| WO | WO 00/68282 | 11/2000 |

OTHER PUBLICATIONS

Presentation "ACP 1234" International Specialty Products, Nov. 2000.

* cited by examiner

*Primary Examiner*—Eisa Elhilo
(74) *Attorney, Agent, or Firm*—Oblon, Spivak, McClelland, Maier & Neustadt, P.C.

(57) ABSTRACT

The invention relates to an oxidation-dyeing composition for keratin fibers, in particular for human keratin fibers and more specifically hair, comprising at least one oxidation dye and a cationic poly(vinyllactam) in a medium suitable for dyeing. The invention also relates to the dyeing methods and devices using said composition.

51 Claims, No Drawings

OXIDATION DYEING COMPOSITION FOR KERATIN FIBERS COMPRISING A CATIONIC POLY(VINYLLACTAM)

The present invention relates to a composition for the oxidation dyeing of keratin fibers, in particular human keratin fibers and more particularly hair, comprising at least one oxidation dye and at least one cationic poly(vinyllactam).

It is known to dye keratin fibers, and in particular human hair, with dyeing compositions containing oxidation dye precursors, generally called "oxidation bases", in particular ortho- or para-phenylenediamines, ortho- or para-aminophenols, and heterocyclic bases.

Oxidation dye precursors are compounds initially only slightly colored or not colored which develop their dyeing power in the hair in the presence of oxidizing agents, leading to the formation of colored compounds. The formation of these colored compounds results either from oxidative condensation of the "oxidation bases" with themselves, or oxidative condensation of the "oxidation bases" with color modifying compounds, or "couplers", which are generally present in the dyeing compositions used in oxidation dyeing and are represented more particularly by meta-phenylenediamines, meta-aminophenols and meta-diphenols, and certain heterocyclic compounds.

The variety of molecules used, which consist, on the one hand, of "oxidation bases" and on the other hand, of "couplers", allows a very rich palette of colors to be obtained.

To confine the oxidation dyeing product upon application to the hair so that it does not run over the face or outside the areas which it is desired to dye, use has up until now been made of traditional thickeners such as crosslinked polyacrylic acid, hydroxyethylcelluloses, certain polyurethanes, waxes or mixtures of nonionic surfactants having an HLB (Hydrophilic Lipophilic Balance), which, suitably chosen, produce a gelling effect when they are diluted with water and/or surfactants.

However, the applicant has observed that the abovementioned thickening systems do not make it possible to obtain intense and chromatic shades of low selectivity and good fastness while offering a good cosmetic condition to the treated hair. Moreover, it has also been observed that the ready-to-use dyeing compositions containing the oxidation dye(s), and the thickening systems of the prior art do not allow a sufficiently precise application without running or drops in viscosity over time.

However, after extensive research carried out on the subject, the applicant has just now discovered that it is possible to obtain ready-to-use oxidation dyeing compositions which do not run and therefore remain well confined to the site of application, and which also make it possible to obtain intense and chromatic (radiant) shades with low selectivities and good fastness towards chemical agents (shampoo, permanent waving and the like) or natural agents (light, perspiration and the like) while offering the hair good cosmetic properties, if there is introduced (i) either into the composition containing the oxidation dye(s) and optionally the coupler(s) [or composition A], or (ii) into the oxidizing composition [or composition B], or (iii) into both compositions at the same time, an effective quantity of a cationic poly(vinyllactam).

These discoveries form the basis of the present invention.

The subject of the present invention is thus a composition for the oxidation dyeing of keratin fibers, in particular human keratin fibers, and in particular hair, comprising, in an appropriate dyeing medium, at least one oxidation dye, which is characterized in that it additionally contains at least one cationic poly(vinyllactam).

Another subject of the invention relates to a ready-to-use composition for dyeing keratin fibers which contains at least one oxidation dye and at least one cationic poly(vinyllactam) as defined below and an oxidizing agent.

The expression "ready-to-use composition" is understood to mean, for the purposes of the invention, the composition intended to be applied as it is to keratin fibers, that is to say that it can be stored as it is before use or be obtained from the fresh mixing of two or more compositions.

The invention also relates to a method for dyeing keratin fibers, and in particular human keratin fibers such as hair, consisting in applying to the fibers at least one composition A containing, in an appropriate dyeing medium, at least one oxidation dye, the color being developed at alkaline, neutral or acidic pH with the aid of a composition B containing at least one oxidizing agent which is mixed just at the time of use with the composition A or which is applied sequentially without intermediate rinsing, at least one cationic poly (vinyllactam) as defined below being present in the composition A or in the composition B or in each of the compositions A and B.

The subject of the invention is also multicompartment dyeing devices or "kits".

A 2-compartment device according to the invention comprises a compartment containing a composition A1 containing, in an appropriate dyeing medium, at least one oxidation dye, and another compartment containing a composition B1 containing, in an appropriate dyeing medium, an oxidizing agent, the cationic poly(vinyllactam) polymer as defined below being present in the composition A1 or the composition B1, or in each of the compositions A1 and B1.

Another device, with 3 compartments according to the invention, comprises a first compartment containing a composition A2 containing, in an appropriate dyeing medium, at least one oxidation dye, a second compartment containing a composition B2 containing, in an appropriate dyeing medium, at least one oxidizing agent, and a third compartment containing a composition C containing, in an appropriate dyeing medium, at least one cationic poly(vinyllactam) polymer as defined below, it being also possible for the composition A2 and/or the composition B2 to contain a cationic poly(vinyllactam) polymer as defined below.

However, other characteristics, aspects, subjects and advantages of the invention will appear more clearly on reading the description and the examples which follow.

Without wishing to be bound by any theory, it would appear that the advantages provided by the cationic poly (vinyllactams) according to the present invention and as defined below are related to a behavior of associative type thickening polymers.

Associative polymers are polymers whose molecules are capable, in the formulation medium, of combining with each other or with molecules of other compounds.

Their chemical structure generally comprises at least one hydrophilic region and at least one hydrophobic region, the hydrophobic region(s) comprising at least one fatty chain.

Cationic Polyvinyllactam Polymers According to the Invention

The cationic poly(vinyllactam) polymers according to the invention comprise:

a) at least one monomer of the vinyllactam or alkylvinyllactam type;

b) at least one monomer having the following structure (I) or (II):

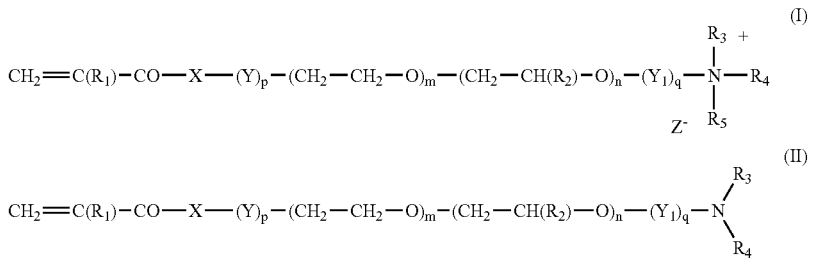

in which:

X denotes an oxygen atom or a radical $NR_6$, $R_1$ and $R_6$ denote, independently of each other, a hydrogen atom or a linear or branched $C_1$–$C_5$ alkyl radical, $R_2$ denotes a linear or branched $C_{1-4}$ alkyl radical, $R_3$, $R_4$ and $R_5$ denote, independently of each other, a hydrogen atom, a linear or branched $C_1$–$C_{30}$ alkyl radical or a radical of formula (III):

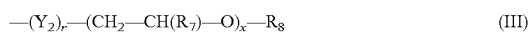

Y, $Y_1$ and $Y_2$ denote, independently of each other, a linear or branched $C_2$–$C_{16}$ alkylene radical, $R_7$ denotes a hydrogen atom, or a linear or branched $C_1$–$C_4$ alkyl radical or a linear or branched $C_1$–$C_4$ hydroxyalkyl radical, $R_8$ denotes a hydrogen atom or a linear or branched $C_1$–$C_{30}$ alkyl radical, p, q and r denote, independently of each other, either the value zero, or the value 1, m and n denote, independently of each other, an integer ranging from 0 to 100, x denotes an integer ranging from 1 to 100, Z denotes an organic or inorganic acid anion, provided that:

at least one of the substituents $R_3$, $R_4$, $R_5$ or $R_8$ denotes a linear or branched $C_9$–$C_{30}$ alkyl radical, if m or n is different from zero, then q is equal to 1, if m or n are equal to zero, then p or q is equal to 0.

The cationic poly(vinyllactam) polymers according to the invention may be crosslinked or noncrosslinked and may also be block polymers.

Preferably, the counterion $Z^-$ of the monomers of formula (I) is chosen from halide ions, phosphate ions, methosulfate ion, tosylate ion.

Preferably, $R_3$, $R_4$ and $R_5$ denote, independently of each other, a hydrogen atom or a linear or branched $C_1$–$C_{30}$ alkyl radical.

More preferably, the monomer b) is a monomer of formula (I) for which, still more preferably, m and n are equal to zero.

The vinyllactam or alkylvinyllactam monomer is preferably a compound having the structure (IV):

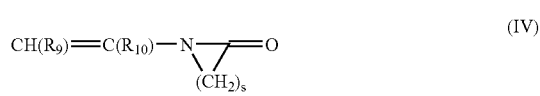

in which:

s denotes an integer ranging from 3 to 6, $R_9$ denotes a hydrogen atom or a $C_1$–$C_5$ alkyl radical, $R_{10}$ denotes a hydrogen atom or a $C_1$–$C_5$ alkyl radical, provided that at least one of the radicals $R_9$ and $R_{10}$ denotes a hydrogen atom.

Still more preferably, the monomer (IV) is vinylpyrrolidone.

The cationic poly(vinyllactam) polymers according to the invention may also contain one or more additional, preferably cationic or nonionic, monomers.

As compounds which are more particularly preferred according to the invention, there may be mentioned the following terpolymers comprising at least:

a)—one monomer of formula (IV), b)—one monomer of formula (I) in which p=1, q=0, $R_3$ and $R_4$ denote, independently of each other, a hydrogen atom or a $C_1$–$C_5$ alkyl radical and $R_5$ denotes a $C_9$–$C_{24}$ alkyl radical, and c)—one monomer of formula (II) in which $R_3$ and $R_4$ denote, independently of each other, a hydrogen atom or a $C_1$–$C_5$ alkyl radical.

Still more preferably, there will be used the terpolymers comprising, by weight, 40 to 95% of monomer (a), 0.1 to 55% of monomer (c) and 0.25 to 50% of monomer (b). Such polymers are described in patent application WO-00/68282 whose content forms an integral part of the invention.

As cationic poly(vinyllactam) polymers according to the invention, there are used in particular the terpolymers vinylpyrrolidone/dimethylaminopropylmethacrylamide/dodecyldimethylmethacrylamidopropylammonium tosylate, the terpolymers vinylpyrrolidone/dimethylaminopropylmethacrylamide/cocoyldimethylmethacrylamidopropylammonium tosylate, the terpolymers vinylpyrrolidone/dimethylaminopropylmethacrylamide/lauryldimethylmethacrylamidopropylammonium tosylate or chloride.

The weight-average molecular mass of the cationic poly(vinyllactam) polymers according to the present invention is preferably between 500 and 20 000 000. It is more particularly between 200 000 and 2 000 000 and still more preferably between 400 000 and 800 000.

In the dyeing composition according to the invention, the cationic poly(vinyllactam) or poly(vinyllactams) described above are preferably used in a quantity which may vary from about 0.01 to 10% by weight of the total weight of the composition. More preferably, this quantity varies from about 0.1 to 5% by weight.

Oxidation Dyes

The oxidation dyes which can be used according to the invention are chosen from oxidation bases and/or couplers.

Preferably, the compositions according to the invention contain at least one oxidation base.

The oxidation bases which can be used in the context of the present invention are chosen from those conventionally known in oxidation dyeing, and among which there may be mentioned in particular ortho- and para-phenylenediamines, double bases, ortho- and para-aminophenols, the following heterocyclic bases as well as their addition salts with an acid.

There may be mentioned in particular:

(A) the para-phenylenediamines of the following formula (V) and their addition salts with an acid:

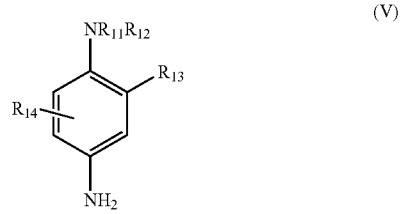

(V)

in which:

$R_{11}$ represents a hydrogen atom, a $C_1$–$C_4$ alkyl radical, a monohydroxy($C_1$–$C_4$ alkyl) radical, a polyhydroxy($C_2$–$C_4$ alkyl) radical, a ($C_1$–$C_4$)alkoxy($C_1$–$C_4$)alkyl radical, a $C_1$–$C_4$ alkyl radical substituted with a nitrogen-containing group, a phenyl radical or a 4'-aminophenyl radical;

$R_{12}$ represents a hydrogen atom, a $C_1$–$C_4$ alkyl radical, a monohydroxy($C_1$–$C_4$ alkyl) radical or a polyhydroxy ($C_2$–$C_4$ alkyl) radical, a ($C_1$–$C_4$)alkoxy($C_1$–$C_4$)alkyl radical or a $C_1$–$C_4$ alkyl radical substituted with a nitrogen-containing group;

$R_{11}$ and $R_{12}$ may also form with the nitrogen atom carrying them a 5- or 6-membered nitrogen-containing heterocycle optionally substituted with one or more alkyl, hydroxyl or ureido groups;

$R_{13}$ represents a hydrogen atom, a halogen atom such as a chlorine atom, a $C_1$–$C_4$ alkyl radical, a sulfo radical, a carboxyl radical, a monohydroxy($C_1$–$C_4$ alkyl) radical or a hydroxy($C_1$–$C_4$ alkoxy) radical, an acetylamino($C_1$–$C_4$ alkoxy) radical, a mesylamino($C_1$–$C_4$ alkoxy) radical or a carbamoylamino($C_1$–$C_4$ alkoxy) radical, $R_{14}$ represents a hydrogen or halogen atom or a $C_1$–$C_4$ alkyl radical.

Among the nitrogen-containing groups of formula (V) above, there may be mentioned in particular the amino, mono($C_1$–$C_4$)alkylamino, ($C_1$–$C_4$)dialkylamino, ($C_1$–$C_4$) trialkylamino, monohydroxy($C_1$–$C_4$)alkylamino, imidazolinium and ammonium radicals.

Among the para-phenylenediamines of formula (V) above, there may be mentioned more particularly para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl) amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 2-methyl-1-N-β-hydroxyethyl-para-phenylenediamine and their addition salts with an acid.

Among the para-phenylenediamines of formula (V) above, there are most particularly preferred para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and their addition salts with an acid.

(B) According to the invention, "double bases" is understood to mean the compounds containing at least two aromatic rings on which amino and/or hydroxyl groups are carried.

Among the double bases which can be used as oxidation bases in the dyeing compositions in accordance with the invention, there may be mentioned in particular the compounds corresponding to the following formula (VI), and their addition salts with an acid:

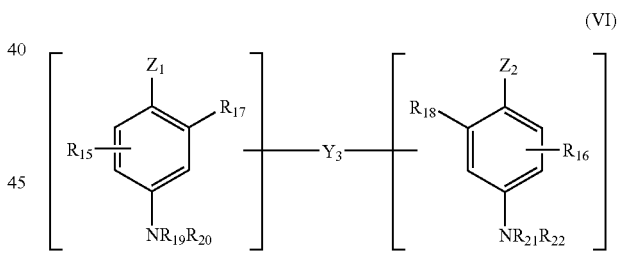

(VI)

in which:

$Z_1$ and $Z_2$, which are identical or different, represent a hydroxyl or —$NH_2$ radical which may be substituted with a $C_1$–$C_4$ alkyl radical or with a linking arm $Y_3$;

the linking arm $Y_3$ represents a linear or branched alkylene chain comprising from 1 to 14 carbon atoms, which may be interrupted by or which may end with one or more nitrogen-containing groups and/or one or more heteroatoms such as oxygen, sulfur or nitrogen atoms, and optionally substituted with one or more hydroxyl or $C_1$–$C_6$ alkoxy radicals;

$R_{15}$ and $R_{16}$ represent a hydrogen or halogen atom, a $C_1$–$C_4$ alkyl radical, a monohydroxy($C_1$–$C_4$ alkyl) radical, a polyhydroxy ($C_2$–$C_4$ alkyl) radical, an amino($C_1$–$C_4$ alkyl) radical or a linking arm $Y_3$;

$R_{17}$, $R_{18}$, $R_{19}$, $R_{20}$, $R_{21}$ and $R_{22}$, which are identical or different, represent a hydrogen atom, a linking arm $Y_3$ or a $C_1$–$C_4$ alkyl radical;

it being understood that the compounds of formula (VI) contain only one linking arm $Y_3$ per molecule.

Among the nitrogen-containing groups of formula (VI) above, there may be mentioned in particular the amino, mono($C_1$–$C_4$)alkylamino, ($C_1$–$C_4$)dialkylamino, ($C_1$–$C_4$) trialkylamino, monohydroxy($C_1$–$C_4$)alkylamino, imidazolinium and ammonium radicals.

Among the double bases of formulae (VI) above, there may be mentioned more particularly N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and their addition salts with an acid.

Among these double bases of formula (VI), N,N'-bis(β-hydroxyethyl)-N,N'-bis(4'-aminophenyl)-1,3-diaminopropanol, 1,8-bis(2,5-diaminophenoxy)-3,5-dioxaoctane or one of their addition salts with an acid are particularly preferred.

(C) the para-aminophenols corresponding to the following formula (VII), and their addition salts with an acid:

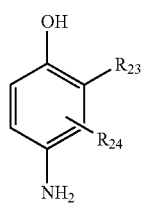

(VII)

in which:

$R_{23}$ represents a hydrogen atom, a halogen atom such as fluorine, a $C_1$–$C_4$ alkyl, monohydroxy($C_1$–$C_4$ alkyl), ($C_1$–$C_4$)alkoxy ($C_1$–$C_4$)alkyl or amino($C_1$–$C_4$ alkyl) or hydroxy($C_1$–$C_4$) alkylamino($C_1$–$C_4$ alkyl) radical, $R_{24}$ represents a hydrogen atom or a halogen atom such as fluorine, a $C_1$–$C_4$ alkyl, monohydroxy($C_1$–$C_4$ alkyl), polyhydroxy($C_2$–$C_4$ alkyl), amino($C_1$–$C_4$ alkyl), cyano ($C_1$–$C_4$ alkyl) or ($C_1$–$C_4$)alkoxy($C_1$–$C_4$)alkyl radical.

Among the para-aminophenols of formula (VII) above, there may be mentioned more particularly para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, and their addition salts with an acid.

(D) the ortho-aminophenols which can be used as oxidation bases in the context of the present invention are in particular chosen from 2-aminophenol, 2-amino-1-hydroxy-5-methylbenzene, 2-amino-1-hydroxy-6-methylbenzene, 5-acetamido-2-aminophenol, and their addition salts with an acid.

(E) among the heterocyclic bases which can be used as oxidation bases in the dyeing compositions in accordance with the invention, there may be mentioned more particularly pyridine derivatives, pyrimidine derivatives, pyrazole derivatives, and their addition salts with an acid.

Among the pyridine derivatives, there may be mentioned more particularly the compounds described for example in Patents GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl) amino-3-amino-6-methoxypyridine, 3,4-diaminopyridine, and their addition salts with an acid.

Among the pyrimidine derivatives, there may be mentioned more particularly the compounds described for example in German Patent DE 2,359,399 or Japanese Patents JP 88-169,571 and JP 91-10659 or Patent Applications WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and the pyrazolopyrimidine derivatives such as those mentioned in Patent Application FR-A-2,750,048 and among which there may be mentioned pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol; 2-[(7-aminopyrazolo[1,5-a]pyrimidin-3-yl)(2-hydroxyethyl) amino]ethanol; 5,6-dimethylpyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine; 3-amino-5-methyl-7-imidazolylpropylaminopyrazolo[1,5-a]pyrimidine; and their addition salts and their tautomeric forms, when a tautomeric equilibrium exists and their addition salts with an acid.

Among the pyrazole derivatives, there may be mentioned more particularly the compounds described in Patents DE 3,843,892, DE 4,133,957 and Patent Applications WO 94/08969, WO 94/08970, FR-A-2,733,749 and DE 195 43 988 such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl) amino-1-methylpyrazole, and their addition salts with an acid.

According to the present invention, the oxidation bases preferably represent from 0.0005 to 12% by weight approximately of the total weight of the composition and more preferably still from 0.005 to 8% by weight approximately of this weight.

The couplers which can be used in the dyeing method according to the invention are those conventionally used in oxidation dyeing compositions, that is to say meta-aminophenols, meta-phenylenediamines, meta-diphenols, naphthols and heterocyclic couplers such as for example indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines and their addition salts with an acid.

These couplers are more particularly chosen from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxy-benzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, 2-amino-3-hydroxypyridine, 3,6-dimethylpyrazolo[3,2-c]-1,2,4-triazole, 2,6-dimethylpyrazolo[1,5-b]-1,2,4-triazole and their addition salts with an acid.

When they are present, these couplers preferably represent from 0.0001 to 10% by weight approximately of the total weight of the composition, and more preferably still from 0.005 to 5% by weight approximately.

In general, the addition salts with an acid of the oxidation bases and couplers are in particular chosen from hydrochlorides, hydrobromides, sulfates and tartrates, lactates and acetates.

The composition according to the invention may also contain, in addition to the oxidation dyes defined above, direct dyes in order to enrich the shades with glints. These direct dyes may then in particular be chosen from neutral, cationic or anionic nitro, azo or anthraquinone dyes in the proportion by weight of about 0.001 to 20% and preferably from 0.01 to 10% of the total weight of the composition.

The composition A and/or the composition B may in addition more particularly contain at least one amphoteric polymer or one cationic polymer different from the cationic poly(vinyllactams) according to the present invention.

Cationic Polymers Different from Those of the Invention

For the purposes of the present invention, the expression "cationic polymer" denotes any polymer containing cationic groups and/or groups which can be ionized to cationic groups.

The cationic polymers which can be used in accordance with the present invention may be chosen from all those already known per se to improve the cosmetic properties of hair, namely in particular those described in Patent Application EP-A-337 354 and in French patents FR-2,270,846, 2,383,660, 2,598,611, 2,470,596 and 2,519,863.

The preferred cationic polymers are chosen from those which contain units comprising primary, secondary, tertiary and/or quaternary amino groups which may either form part of the principal polymeric chain, or which may be carried by a side substituent directly linked thereto.

The cationic polymers used generally have a number-average molecular mass of between 500 and $5 \times 10^6$ approximately, and preferably between $10^3$ and $3.10^6$ approximately.

Among the cationic polymers, there may be mentioned more particularly the polymers of the polyamine, polyamino amide and quaternary polyammonium type.

They are known products. They are described in particular in French patents No. 2,505,348 or 2,542,997. Among said polymers, there may be mentioned:

(1) the homopolymers or copolymers derived from acrylic or methacrylic esters or amides and comprising at least one of the units of the following formulae (VIII), (IX), (X) and (XI):

(VIII)

(IX)

(X)

(XI)

in which:

$R_{33}$, which are identical or different, denote a hydrogen atom or a $CH_3$ radical;

A, which are identical or different, represent a linear or branched alkyl group of 1 to 6 carbon atoms, preferably 2 or 3 carbon atoms or a hydroxyalkyl group of 1 to 4 carbon atoms;

$R_{34}$, $R_{35}$, and $R_{36}$, which are identical or different, represent an alkyl group having from 1 to 18 carbon atoms or a benzyl radical and preferably an alkyl group having from 1 to 6 carbon atoms;

$R_{31}$ and $R_{32}$, which are identical or different, represent hydrogen or an alkyl group having from 1 to 6 carbon atoms and preferably methyl or ethyl;

X, denotes an anion derived from an inorganic or organic acid such as a methosulfate anion or a halide such as chloride or bromide.

The polymers of the family (1) may contain, in addition, one or more units derived from comonomers which may be chosen from the family of acrylamides, methacrylamides, diacetone acrylamides, acrylamides and methacrylamides substituted on the nitrogen with lower ($C_1$–$C_4$)alkyls, acrylic or methacrylic acids or esters thereof, vinyllactams such as vinylpyrrolidone or vinylcaprolactam, vinyl esters.

Thus, among these polymers of the family (1), there may be mentioned:

the copolymers of acrylamide and dimethylamino-ethyl methacrylate quaternized with dimethyl sulfate or with a dimethyl halide such as that sold under the name HERCOFLOC® by the company HERCULES, the copolymers of acrylamide and methacryloyloxyethyltrimethylammonium chloride described, for example, in Patent Application EP-A-080976 and sold under the name BINA QUAT P 100 by the company CIBA GEIGY, the copolymer of acrylamide and methacryloyloxyethyltrimethylammonium methosulfate sold under the name RETEN® by the company HERCULES, the vinylpyrrolidone/dialkylaminoalkyl acrylate or methacrylate copolymers, quaternized or otherwise, such as the products sold under the name "GAFQUAT®" by the company ISP such as for example "GAFQUAT 734" or "GAFQUAT 755" or alternatively the products called "COPOLYMER 845®, 958® and 937®". These polymers are described in detail in French Patents 2,077,143 and 2,393,573, the dimethylaminoethyl methacrylate/vinylcaprolactam/vinylpyrrolidone terpolymers such as the product sold under the name GAFFIX VC 713® by the company ISP, the vinylpyrrolidone/methacrylamidopropyldimethylamine copolymers marketed in particular under the name STYLEZE CC 10® by ISP, and the quaternized vinylpyrrolidone/dimethyl-aminopropyl methacrylamide copolymers such as the product sold under the name "GAFQUAT® HS 100" by the company ISP.

(2) The cellulose ether derivatives comprising quaternary ammonium groups, described in French Patent 1,492,597, and in particular the polymers marketed under the names "JR®" (JR 400, JR 125, JR 30M) or "LR®" (LR 400, LR 30M) by the company Union Carbide Corporation. These polymers are also defined in the CTFA dictionary as hydroxyethyl cellulose quaternary ammoniums which have reacted with an epoxide substituted by a trimethylammonium group.

(3) Cationic cellulose derivatives such as cellulose copolymers or cellulose derivatives grafted with a quaternary ammonium water-soluble monomer, and described especially in U.S. Pat. No. 4,131,576, such as hydroxyalkyl celluloses like hydroxymethyl, hydroxyethyl or hydroxypropyl celluloses grafted especially with a methacryloylethyltrimethylammonium, methacrylamidopropyltrimethylammonium or dimethyldiallylammonium salt.

The commercialized products corresponding to this definition are more particularly the products sold under the name "Celquat® L 200" and "Celquat® H 100" by the company National Starch.

(4) The cationic polysaccharides described more particularly in U.S. Pat. Nos. 3,589,578 and 4,031,307 such as guar gums containing cationic trialkylammonium groups. Guar gums modified with a 2,3-epoxypropyltri-methylammonium salt (e.g. chloride) are for example used.

Such products are marketed in particular under the trade names JAGUAR® C13 S, JAGUAR® C 15, JAGUAR® C 17 or JAGUAR® C162 by the company MEYHALL.

(5) Polymers consisting of piperazinyl units and of alkylene or hydroxyalkylene divalent radicals with straight or branched chains, optionally interrupted by oxygen, sulfur or nitrogen atoms or by aromatic or heterocyclic rings, as well as the oxidation and/or quaternization products of these polymers. Such polymers are described especially in French patents 2,162,025 and 2,280,361.

(6) Water-soluble polyaminoamides prepared in particular by polycondensation of an acid compound with a polyamine; these polyaminoamides may be crosslinked with an epihalohydrin, a diepoxide, a dianhydride, an unsaturated dianhydride, a diunsaturated derivative, a bishalohydrin, a bisazetidinium, a bishaloacyldiamine, an alkylbishalide or else with an oligomer resulting from the reaction of a difunctional compound which is reactive towards a bishalohydrin, a bisazetidinium, a bishaloacyldiamine, an alkylbishalide, an epihalohydrin, a diepoxide or a diunsaturated derivative; the crosslinking agent being employed in proportions ranging from 0.025 to 0.35 mol per amine group of the polyaminoamide; these polyaminoamides may be alkylated or, if they include one or more tertiary amine functional groups, quaternized. Such polymers are described especially in French Patents 2,252,840 and 2,368,508.

(7) Polyaminoamide derivatives resulting from the condensation of polyalkylenepolyamines with polycarboxylic acids, followed by an alkylation with difunctional agents. There may be mentioned, for example, the adipic acid—dialkylaminohydroxyalkyldialkylenetriamine polymers in which the alkyl radical contains from 1 to 4 carbon atoms and preferably denotes methyl, ethyl or propyl. Such polymers are described especially in French Patent 1,583,363.

Among these derivatives there may be mentioned more particularly the adipic acid/dimethylaminohydroxypropyl/diethylenetriamine polymers sold under the name "Cartaretine® F, F4 or F8" by the company Sandoz.

(8) Polymers obtained by reaction of a polyalkylenepolyamine containing two primary amine groups and at least one secondary amine group with a dicarboxylic acid chosen from diglycolic acid and saturated aliphatic dicarboxylic acids containing from 3 to 8 carbon atoms. The molar ratio of the polyalkylenepolyamine to the dicarboxylic acid being between 0.8:1 and 1.4:1; the polyaminoamide resulting therefrom being made to react with epichlorohydrin in a molar ratio of epichlorohydrin relative to the secondary amine group of the polyaminoamide of between 0.5:1 and 1.8:1. Such polymers are described especially in U.S. Pat. Nos. 3,227,615 and 2,961,347.

Polymers of this type are marketed in particular under the name "Hercosett® 57" by the company Hercules Inc. or else under the name of "PD 170®" or "Delsette 101®" by the company Hercules in the case of the copolymer of adipic acid/epoxypropyl/diethylene-triamine.

(9) Cyclopolymers of alkyldiallylamine or of dialkyldiallylammonium, such as the homopolymers or copolymers comprising, as main constituent of the chain, units chosen from those corresponding to the formulae (XII) and (XIII):

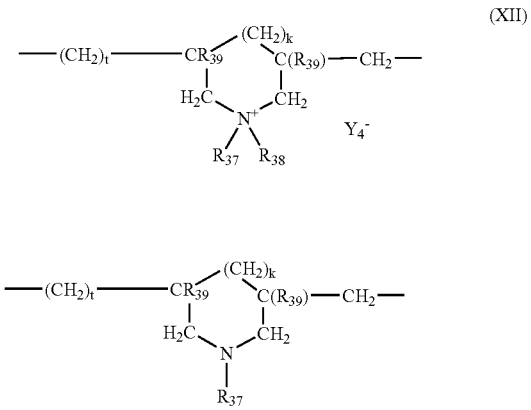

in which formulae k and t are equal to 0 or 1, the sum k+t being equal to 1; $R_{39}$ denotes a hydrogen atom or a methyl radical; $R_{37}$ and $R_{38}$, independently of each other, denote an alkyl group containing from 1 to 22 carbon atoms, a hydroxyalkyl group in which the alkyl group preferably has 1 to 5 carbon atoms, or a lower ($C_1$–$C_4$)amidoalkyl group or $R_{37}$ and $R_{38}$ may denote, jointly with the nitrogen atom to which they are attached, heterocyclic groups such as piperidinyl or morpholinyl; $R_{37}$ and $R_{38}$, independently of each other, preferably denote an alkyl group having 1 to 4 carbon atoms; $Y_4^-$ is an anion such as bromide, chloride, acetate, borate, citrate, tartrate, bisulfate, bisulfite, sulfate or phosphate. These polymers are described especially in French Patent 2,080,759 and in its certificate of addition 2,190,406.

Among the polymers defined above there may be mentioned more particularly the dimethyldiallylammonium chloride homopolymer sold under the name "Merquat® 100" by the company Calgon (and its homologs of low weight-average molecular masses) and the copolymers of diallyl-dimethylammonium chloride and acrylamide marketed under the name "MERQUAT® 550".

(10) The quaternary diammonium polymer containing repeat units corresponding to the formula (XIV):

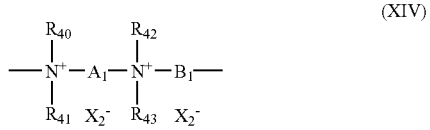

in which:

$R_{40}$, $R_{41}$, $R_{42}$ and $R_{43}$, which are identical or different, represent aliphatic, alicyclic or arylaliphatic radicals containing from 1 to 20 carbon atoms or lower hydroxyalkyl aliphatic radicals, or else $R_{10}$, $R_{11}$, $R_{12}$ and $R_{13}$, together or separately, form, with the nitrogen atoms to which they are attached, heterocyclic rings optionally containing a second heteroatom other than nitrogen, or else $R_{40}$, $R_{41}$, $R_{42}$ and $R_{43}$ denote a linear or branched $C_1$–$C_6$ alkyl radical substituted by a nitrile, ester, acyl, amide or —CO—O—$R_{44}$-$D_1$ or —CO—NH—$R_{44}$-$D_1$ group where $R_{44}$ is an alkylene and $D_1$ a quaternary ammonium group;

$A_1$ and $B_1$ represent polymethylene groups containing from 2 to 20 carbon atoms which may be linear or branched, saturated or unsaturated and which may contain, bonded to or inserted into the main chain, one or more aromatic rings, or one or more oxygen or sulfur atoms or sulfoxide, sulfone, disulfide, amino, alkylamino, hydroxyl, quaternary ammonium, ureido, amide or ester groups, and $X_2^-$ denotes an anion derived from an inorganic or organic acid;

$A_1$, $R_{40}$ and $R_{42}$, with the two nitrogen atoms to which they are attached, may form a piperazine ring; in addition if $A_1$ denotes a saturated or unsaturated, linear or branched alkylene or hydroxyalkylene radical, $B_1$ may also denote a group —$(CH_2)_{n1}$—CO—$D_2$—OC—$(CH_2)_{n1}$— in which $n_1$ is between 1 and 100, and preferably between 1 and 50, and $D_2$ denotes:

a) a glycol residue of formula: —O-$Z_3$-O—, where $Z_3$ denotes a linear or branched hydrocarbon radical or a group corresponding to one of the following formulae:

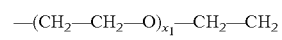

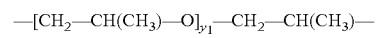

where $x_1$ and $y_1$ denote an integer from 1 to 4, representing a defined and unique degree of polymerization or any number from 1 to 4 representing a mean degree of polymerization;

b) a disecondary diamine residue such as a piperazine derivative;

c) a diprimary diamine residue of formula: —NH—$Y_5$—NH—, where $Y_5$ denotes a linear or branched hydrocarbon radical or else the divalent radical

d) a ureylene group of formula: —NH—CO—NH—;

$X_2^-$ is preferably an anion such as chloride or bromide.

These polymers have a number-average molecular mass which is generally between 1000 and 100 000.

Polymers of this type are described especially in French Patents 2,320,330, 2,270,846, 2,316,271, 2,336,434 and 2,413,907 and U.S. Pat. Nos. 2,273,780, 2,375,853, 2,388, 614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is possible to use more particularly the polymers which consist of repeat units corresponding to the following formula (XV):

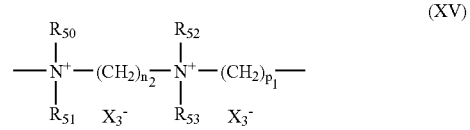

in which $R_{50}$, $R_{51}$, $R_{52}$ and $R_{53}$, which are identical or different, denote an alkyl or hydroxyalkyl radical having from 1 to 4 carbon atoms approximately, $n_2$ and $p_1$ are integers varying from 2 to 20 approximately and $X_3^-$ is an anion derived from an inorganic or organic acid.

(11) The quaternary polyammonium polymers consisting of recurring units of formula (XVI):

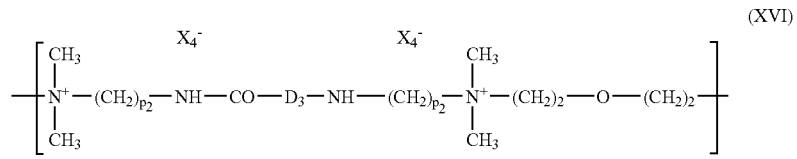

(XVI)

in which $p_2$ denotes an integer varying from 1 to 6 approximately, $D_3$ may be zero or may represent a group —$(CH_2)_{r1}$—CO— in which $r_1$ denotes a number equal to 4 or to 7, $X_4^-$ is an anion.

Such polymers may be prepared according to the methods described in U.S. Pat. Nos. 4,157,388, 4,702,906, 4,719,282. They are in particular described in Patent Application EP-A-122 324.

Among these, there may be mentioned for example the products "Mirapol® A 15", "Mirapol® AD1", "Mirapol® AZ1" and "Mirapol® 175" sold by the company Miranol.

(12) Quaternary vinylpyrrolidone and vinylimidazole polymers such as, for example, the products marketed under the names Luviquat® FC 905, FC 550 and FC 370 by the company B.A.S.F.

(13) Polyamines like the Polyquart H sold by Henkel, referenced under the name of "Polyethylene Glycol (15) Tallow Polyamine" in the CTFA dictionary.

(14) The crosslinked polymers of methacryloyloxy($C_1$–$C_4$ alkyl)tri($C_1$–$C_4$ alkyl)ammonium salts such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. More particularly, it is possible to employ a crosslinked acrylamide/methacryloyloxyethyltrimethylammonium chloride copolymer (20/80 by weight) in the form of a dispersion containing 50% by weight of said copolymer in mineral oil. This dispersion is marketed under the name of "SALCARE® SC 92" by the company ALLIED COLLOIDS. It is also possible to employ a crosslinked methacryloyloxyethyltrimethylammonium chloride homopolymer containing approximately 50% by weight of the homopolymer in mineral oil or in a liquid ester. These dispersions are marketed under the names of "SALCARE® SC 95" and "SALCARE® SC 96" by the company ALLIED COLLOIDS.

Other cationic polymers that may be employed within the scope of the invention are polyalkyleneimines, in particular polyethyleneimines, polymers containing vinylpyridine or vinylpyridinium units, condensates of polyamines and of epichlorohydrin, quaternary polyureylenes and chitin derivatives.

Among all the cationic polymers which may be used in the context of the present invention, it is preferable to use the polymers of the families (1), (9), (10), (11) and (14) and more preferably still the polymers with the recurring units of the following formulae (W) and (U):

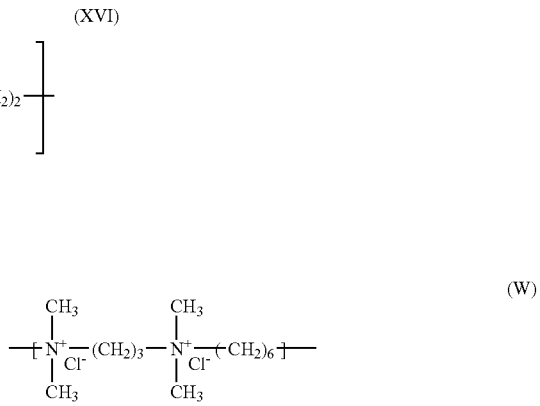

and in particular those whose molecular weight, determined by gel permeation chromatography, is between 9500 and 9900;

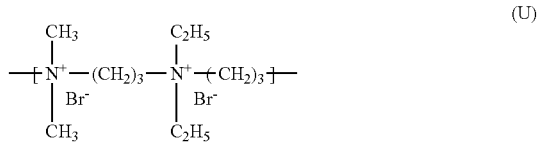

and in particular those whose molecular weight, determined by gel permeation chromatography, is about 1200.

The additional cationic polymer(s) concentration in the composition according to the present invention may vary from 0.01 to 10% by weight relative to the total weight of the composition, preferably from 0.05 to 5% and more preferably still from 0.1 to 3%.

Amphoteric Polymers

The amphoteric polymers which can be used in accordance with the present invention may be chosen from the polymers containing K and M units distributed statistically in the polymer chain where K denotes a unit which is derived from a monomer containing at least one basic nitrogen atom and M denotes a unit which is derived from an acidic monomer containing one or more carboxylic or sulfonic groups or alternatively K and M may denote groups which are derived from zwitterionic monomers of carboxybetaines or of sulfobetaines;

K and M may also denote a cationic polymer chain containing primary, secondary, tertiary or quaternary amine groups, in which at least one of the amine groups carries a carboxylic or sulfonic group linked via a hydrocarbon radical or alternatively K and M form part of a chain of a polymer with an α,β-dicarboxylic ethylene unit in which one of the carboxylic groups has been caused to react with a polyamine containing one or more primary or secondary amine groups.

The amphoteric polymers corresponding to the definition given above which are more particularly preferred are chosen from the following polymers:

1) The polymers resulting from the copolymerization of a monomer derived from a vinyl compound carrying a carboxylic group such as more particularly acrylic acid, methacrylic acid, maleic acid, alpha-chloroacrylic acid, and of a basic monomer derived from a substituted vinyl compound containing at least one basic atom such as more particularly dialkylaminoalkyl methacrylate and acrylate, dialkylaminoalkylmethacrylamide and acrylamide. Such compounds are described in U.S. Pat. No. 3,836,537. Mention may also be made of the sodium acrylate/acryamidopropyltrimethylammonium chloride copolymer sold under the name POLYQUART KE® 3033 by the company HENKEL.

The vinyl compound may also be a dialkyldiallylammonium salt such as dimethyldiallylammonium chloride. The copolymers of acrylic and of the latter monomer are offered under the names MERQUAT® 280, MERQUAT® 295 and MERQUAT® PLUS 3330 by the company CALGON.

(2) The polymers containing units which are derived from:

a) at least one monomer chosen from acrylamides or methacrylamides substituted on the nitrogen by an alkyl radical, b) at least one acidic comonomer containing one or more reactive carboxylic groups, and c) at least one basic comonomer such as esters with primary, secondary, tertiary and quaternary amine substituents of acrylic and methacrylic acids and the product of quaternization of dimethylaminoethyl methacrylate with dimethyl or diethyl sulfate.

The N-substituted acrylamides or methacrylamides more particularly preferred according to the invention are groups whose alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide as well as the corresponding methacrylamides.

The acidic comonomers are chosen more particularly from acrylic, methacrylic, crotonic, itaconic, maleic and fumaric acids as well as the alkyl monoesters having 1 to 4 carbon atoms of maleic or fumaric anhydrides or acids.

The basic comonomers preferred are methacrylates of aminoethyl, butylaminoethyl, N,N'-dimethylaminoethyl, N-tert-butylaminoethyl.

Particularly used are the copolymers whose CTFA name (4th ed. 1991) is Octylacrylamide/acrylates/butylaminoethylmethacrylate copolymer such as the products sold under the name AMPHOMER® or LOVOCRYL® 47 by the company NATIONAL STARCH.

(3) The partially or completely alkylated and crosslinked polyaminoamides derived from polyaminoamides of general formula:

(XVII)

in which $R_{54}$ represents a divalent radical derived from a saturated dicarboxylic acid, a mono- or dicarboxylic aliphatic acid with ethylenic double bond, an ester of a lower alkanol having 1 to 6 carbon atoms of these acids or a radical which is derived from the addition of any one of said acids with a bis-primary or bis-secondary amine, and $Z_4$ denotes a radical of a bis-primary, mono- or bis-secondary polyalkylene-polyamine and preferably represents:

a) in the proportions of 60 to 100 mol %, the radical

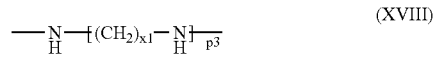

(XVIII)

where $x_1=2$ and $p_3=2$ or 3, or alternatively $x_1=3$ and $p_3=2$, this radical being derived from the diethylenetriamine, triethylenetetraamine or dipropylenetriamine;

b) in the proportions of 0 to 40 mol %, the radical (XVIII) above, in which $x_1=2$ and $p_3=1$ and which is derived from ethylenediamine, or the radical which is derived from piperazine:

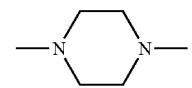

c) in the proportions of 0 to 20 mol %, the radical —NH—$(CH_2)_6$—NH— which is derived from hexamethylenediamine, these polyaminoamines being crosslinked by adding a bifunctional crosslinking agent chosen from the epihalohydrins, diepoxides, dianhydrides, bis-unsaturated derivatives, by means of 0.025 to 0.35 mol of crosslinking agent per amine group of the polyaminoamide and alkylated by the action of acrylic acid, chloroacetic acid or of an alkanesultone or of their salts.

The saturated carboxylic acids are preferably chosen from the acids having 6 to 10 carbon atoms such as adipic, 2,2,4-trimethyladipic and 2,4,4-trimethyladipic acid, terephthalic acid, the acids with an ethylene double bond such as for example acrylic, methacrylic and itaconic acids.

The alkanesultones used in the alkylation are preferably propane or butanesultone, the salts of the alkylating agents are preferably the sodium or potassium salts.

4) The polymers containing zwitterionic units of formula:

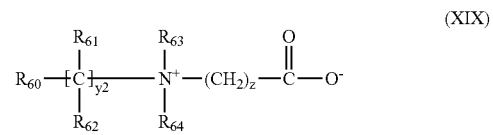

(XIX)

in which $R_{60}$ denotes a polymerizable unsaturated group such as an acrylate, methacrylate, acrylamide or methacrylamide group, $y_2$ and z represent an integer from 1 to 3, $R_{61}$ and $R_{62}$ represent a hydrogen atom, methyl, ethyl or propyl, $R_{63}$ and $R_{64}$ represent a hydrogen atom or an alkyl radical such that the sum of the carbon atoms in $R_{63}$ and $R_{64}$ does not exceed 10.

The polymers comprising such units may also comprise units derived from nonzwitterionic monomers such as dimethyl or diethylaminoethyl acrylate or methacrylate or alkyl acrylates or methacrylates, acrylamides or methacrylamides or vinyl acetate.

By way of example, there may be mentioned the copolymer of butyl methacrylate/dimethylcarboxy-methylammonioethyl methacrylate such as the product sold under the name DIAFORMER Z301® by the company SANDOZ.

(5) The polymers derived from chitosan containing monomeric units corresponding to the following formulae (XX), (XXI), and (XXII):

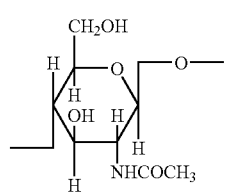

(XX)

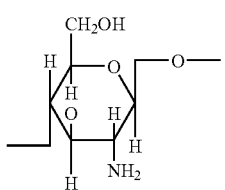

(XXI)

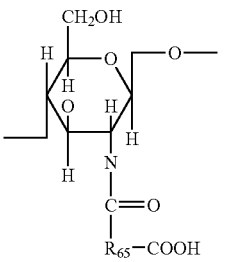

(XXII)

the (XX) unit being present in proportions of between 0 and 30%, the (XXI) unit in proportions of between 5 and 50% and the (XXII) unit in proportions of between 30 and 90%, it being understood that in this (XXII) unit, $R_{65}$ represents a radical of formula:

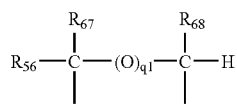

in which $q_1$ denotes zero or 1;

if $q_1=0$, $R_{66}$, $R_{67}$ and $R_{68}$, which are identical or different, each represent a hydrogen atom, a methyl, hydroxyl, acetoxy or amino residue, a monoalkylamine residue or a dialkylamine residue optionally interrupted by one or more nitrogen atoms and/or optionally substituted with one or more amine, hydroxyl, carboxyl, alkylthio or sulfonic groups, or an alkylthio residue whose alkyl group carries an amino residue, at least one of the $R_{26}$, $R_{27}$ and $R_{28}$ radicals being in this case a hydrogen atom; or if $q_1=1$, $R_{66}$, $R_{67}$ and $R_{68}$ each represent a hydrogen atom, as well as the salts formed by these compounds with bases or acids.

(6) The polymers derived from the N-carboxyalkylation of chitosan such as N-carboxymethyl chitosan or N-carboxybutyl chitosan sold under the name "EVALSAN®" by the company JAN DEKKER.

(7) The polymers corresponding to the general formula (XXIII) as described for example in French Patent 1,400,366:

(XXIII)

in which $R_{69}$ represents a hydrogen atom, a $CH_3O$, $CH_3CH_2O$ or phenyl radical, $R_{70}$ denotes hydrogen or a lower alkyl radical such as methyl or ethyl, $R_{71}$ denotes hydrogen or a lower alkyl radical such as methyl or ethyl, $R_{72}$ denotes a lower alkyl radical such as methyl or ethyl or a radical corresponding to the formula: $—R_{73}—N(R_{71})_2$, $R_{73}$ representing a group $—CH_2—CH_2—$, $—CH_2—CH_2—CH_2—$ or $—CH_2—CH(CH_3)—$, $R_{71}$ having the meanings mentioned above, as well as the higher homologs of these radicals and containing up to 6 carbon atoms $r_1$ is such that the molecular weight is from 500 to 6 000 000 and preferably from 1000 to 1 000 000.

(8) Amphoteric polymers of the -D-$X^1$-D-$X^1$-type chosen from:

a) the polymers obtained by the action of chloroacetic acid or sodium chloroacetate on the compounds containing at least one unit of formula:

-D-$X^1$-D-$X^1$-D-     (XXIV)

where D denotes a radical

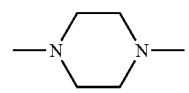

and $X^1$ denotes the symbol E or E', E or E', which are identical or different, denote a bivalent radical which is an alkylene radical with a linear or branched chain containing up to 7 carbon atoms in the principal chain which is unsubstituted or substituted with hydroxyl groups and which may contain, in addition, oxygen, nitrogen or sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, or hydroxyl, benzylamine, amine oxide, quaternary ammonium, amide, imide, alcohol, ester and/or urethane groups;

b) The polymers of formula:

-D-$X^1$-D-$X^1$-     (XXV)

where D denotes a radical

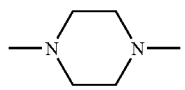

and $X^1$ denotes the symbol E or E' and, at least once, E'; E having the meaning indicated above and E' is a bivalent radical which is an alkylene radical with a linear or branched chain having up to 7 carbon atoms in the principal chain, which is unsubstituted or substituted with one or more hydroxyl radicals and containing one or more nitrogen atoms, the nitrogen atom being substituted with an alkyl chain optionally interrupted by an oxygen atom and necessarily containing one or more carboxyl functional groups or one or more hydroxyl functional groups and betainized by reaction with chloroacetic acid or sodium chloroacetate.

(9) The copolymers $(C_1–C_5)$alkyl vinyl ether/maleic anhydride partially modified by semiamidation with an N,N-dialkylaminoalkylamine such as N,N-dimethylaminopropylamine or by semiesterification with an N,N-dialkanolamine. These copolymers may also contain other vinyl comonomers such as vinylcaprolactam.

The amphoteric polymers particularly preferred according to the invention are those of the family (1).

According to the invention, the additional amphoteric polymer(s) may represent from 0.01% to 10% by weight, preferably from 0.05% to 5% by weight, and still more preferably from 0.1% to 3% by weight, of the total weight of the composition.

The compositions of the invention preferably comprise one or more surfactants.

The surfactant(s) may be equally well chosen, alone or in the form of mixtures, from anionic, amphoteric, nonionic, zwitterionic and cationic surfactants.

The surfactants which are suitable for carrying out the present invention are in particular the following:

(i) Anionic Surfactant(s):

By way of example of anionic surfactants which can be used, alone or as mixtures, in the context of the present invention there may be mentioned in particular (nonlimiting list) the salts (in particular alkali metal, especially sodium, salts, ammonium salts, amine salts, amino alcohol salts or magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamidesulfonates, alkyl aryl sulfonates, α-olefinsulfonates, paraffinsulfonates; $(C_6–C_{24})$ alkyl sulfosuccinates, $(C_6–C_{24})$alkyl ether sulfosuccinates, $(C6–C_{24})$alkylamide sulfosuccinates; $(C_6–C_{24})$alkyl sulfoacetates; $(C6–C_{24})$acyl sarcosinates and $(C_6–C_{24})$acyl glutamates. It is also possible to use $(C_6–C_{24})$alkyl polylycoside carboxylic esters such as alkyl glucoside citrates, alkyl polyglycoside tartrate and alkyl polyglycoside sulfosuccinates, alkyl sulfosuccinamates; acyl isethionates and N-acyltaurates, the alkyl or acyl radical of all these various compounds preferably comprising from 12 to 20 carbon atoms, and the aryl radical preferably denoting a phenyl or benzyl group. Among the anionic surfactants which can still be used, there may also be mentioned the salts of fatty acids such as the salts of oleic, ricinoleic, palmitic and stearic acids, the acids of copra oil or of hydrogenated copra oil; the acyllactylates whose acyl radical comprises 8 to 20 carbon atoms. It is also possible to use the alkyl D-galactoside uronic acids and their salts, the polyoxyalkylenated $(C_6–C_{24})$alkyl ether carboxylic acids, the polyoxyalkylenated $(C_6–C_{24})$alkylaryl ether carboxylic acids, the polyoxyalkylenated $(C_6–C_{24})$alkyl amido ether carboxylic acids and salts thereof, in particular those comprising from 2 to 50 alkylene, in particular ethylene, oxide groups, and mixtures thereof.

(ii) Nonionic Surfactant(s):

The nonionic surfactants themselves are also compounds which are well known per se (in this respect see especially the "Handbook of Surfactants" by M. R. Porter, published by Blackie & Son (Glasgow and London), 1991, pp. 116–178) and, in the context of the present invention, their nature does not assume any critical character. They can thus be chosen especially from (nonlimiting list) alcohols, alpha-diols or polyethoxylated or polypropoxylated alkylphenols which have a fatty chain containing, for example, 8 to 18 carbon atoms, it being possible for the number of ethylene oxide or propylene oxide groups to range especially from 2 to 50. The copolymers of ethylene oxide and propylene oxide and the condensates of ethylene oxide and propylene oxide with fatty alcohols may also be mentioned; the polyethoxylated fatty amides preferably containing from 2 to 30 mol of ethylene oxide, the polyglycerolated fatty amides containing on average 1 to 5 glycerol groups and in particular 1.5 to 4; the polyethoxylated fatty amines preferably containing 2 to 30 mol of ethylene oxide; the oxyethylenated fatty acid esters of sorbitan containing from 2 to 30 mol of ethylene oxide; the fatty acid esters of sucrose, the fatty acid esters of polyethylene glycol, alkylpolyglycosides, the N-alkylglucamine derivatives, amine oxides such as the oxides of $(C_{10}–C_{14})$-alkylamines or the N-acylaminopropylmorpholine oxides.

(iii) Amphoteric or Zwitterionic Surfactant(s):

The amphoteric or zwitterionic surfactants, the nature of which is not of critical importance in the context of the present invention, may be especially (nonlimiting list) derivatives of aliphatic secondary or tertiary amines in which the aliphatic radical is a linear or branched chain containing 8 to 18 carbon atoms and containing at least one water-solubilizing anionic group (for example carboxylate, sulfonate, sulfate, phosphate or phosphonate); $(C_8–C_{20})$ alkylbetaines, sulfobetaines, $(C_8–C_{20})$alkylamido$(C_1–C_6)$ alkylbetaines or $(C_8–C_{20})$alkylamido$(C_1–C_6)$alkylsulfobetaines may further be mentioned.

Among the amine derivatives, there may be mentioned the products sold under the name MIRANOL, as described in patents U.S. Pat. No. 2,528,378 and U.S. Pat. No. 2,781,354 and classified in the CTFA dictionary, 3rd edition, 1982, under the names Amphocarboxyglycinates and Amphocarboxypropionates having the respective structures:

$$R_{82}—CONHCH_2CH_2—N^+(R_{83})(R_{84})(CH_2COO^-)$$

in which: $R_{82}$ denotes an alkyl radical of an acid $R_{82}$—COOH present in hydrolysed copra oil, a heptyl, nonyl or undecyl radical, $R_{83}$ denotes a beta-hydroxyethyl group and $R_{84}$ a carboxymethyl group; and $$R_2'—CONHCH_2CH_2—N(B)(C)$$

in which:

B represents —$CH_2CH_2OX'$, C represents —$(CH_2)_z$—Y', with z=1 or 2,

X' denotes the —$CH_2CH_2$—COOH group or a hydrogen atom

Y' denotes —COOH or the radical —$CH_2$—CHOH—$SO_3H$ $R_2'$ denotes an alkyl radical of an acid $R_2'$—COOH present in copra oil or in hydrolysed linseed oil, an alkyl radical, especially $C_7$, $C_9$, $C_{11}$ or $C_{13}$, a $C_{17}$ alkyl radical and its iso form or an unsaturated $C_{17}$ radical.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylampho-dipropionate, Disodium Capryloamphodipropionate, Lauro-amphodipropionic acid, Cocoamphodipropionic acid.

By way of example, there may be mentioned the cocoamphodiacetate marketed under the trade name MIRANOL® C2M concentrated by the company RHODIA CHIMIE.

(iv) Cationic Surfactants:

Among the cationic surfactants, there may be mentioned in particular (nonlimiting list): the salts of optionally polyoxyalkylenated primary, secondary or tertiary amines; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives or amine oxides of a cationic nature.

The quantities of surfactants present in the composition according to the invention may vary from 0.01 to 40% and preferably from 0.5 to 30% of the total weight of the composition.

Additional Thickening Agents

The compositions according to the invention may also contain other rheology adjusting agents such as cellulosic thickeners (hydroxyethylcellulose, hydroxypropylcellulose, carboxymethylcellulose, and the like), guar gum and its derivatives (hydroxypropylguar and the like), gums of microbial origin (xanthan gum, scleroglucan gum, and the like), synthetic thickeners such as crosslinked homopolymers of acrylic acid and acrylamidopropanesulfonic acid and ionic or nonionic associative polymers such as the polymers marketed under the names PEMULEN® TR1 or TR2 by the company GOODRICH, SALCARE® SC90 by the company ALLIED COLLOIDS, ACULYN® 22, 28, 33, 44 or 46 by the company ROHM & HAAS and ELFACOS® T210 and T212 by the company AKZO.

These supplementary thickeners may represent from 0.01 to 10% by weight of the total weight of the composition.

The appropriate dyeing medium for the composition is preferably an aqueous medium consisting of water and may advantageously contain cosmetically acceptable organic solvents including more particularly alcohols such as ethyl alcohol, isopropyl alcohol, benzyl alcohol and phenylethyl alcohol, glycols or glycol ethers such as, for example, monomethyl, monoethyl and monobutyl ethers of ethylene glycol, propylene glycol or its ethers such as, for example, monomethyl ether of propylene glycol, butylene glycol, dipropylene glycol as well as the alkyl ethers of diethylene glycol such as for example monoethyl ether or monobutyl ether of diethylene glycol. The solvents may then be present in concentrations ranging from about 0.5 to 20% and preferably from about 2 to 10% by weight relative to the total weight of the composition.

The composition A may also contain an effective quantity of other agents, moreover previously known in oxidation dyeing, such as various customary adjuvants such as sequestrants such as EDTA and etidronic acid, UV-screening agents, waxes, volatile or nonvolatile silicones which are cyclic or linear or branched, organomodified (in particular with amine groups) or otherwise, preservatives, ceramides, pseudoceramides, vegetable, mineral or synthetic oils, vitamins or provitamins such as panthenol, opacifiers, associative polymers other than those of the present invention, and in particular nonionic associative polyether-polyurethanes.

Said composition may also contain reducing agents or antioxidants. These may be chosen in particular from sodium sulfite, thioglycolic acid, thiolactic acid, sodium bisulfite, dehydroascorbic acid, hydroquinone, 2-methylhydroquinone, tert-butylhydroquinone and homogentisic acid, and they are then generally present in quantities ranging from about 0.05 to 3% by weight relative to the total weight of the composition.

Of course persons skilled in the art will be careful to choose the possible additional compound(s) mentioned above so that the advantageous properties intrinsically attached to the dyeing composition according to the invention are not, or substantially not, impaired by the envisaged addition(s).

In the ready-to-use composition or in the composition B, the oxidizing agent is preferably chosen from urea peroxide, alkali metal bromates or ferricyanides, persalts such as perborates and persulfates. The use of hydrogen peroxide is particularly preferred. This oxidizing agent advantageously consists of a solution of hydrogen peroxide whose titre may vary more particularly from about 1 to 40 volumes, and still more preferably from about 5 to 40.

It is also possible to use as oxidizing agent one or more oxidation-reduction enzymes such as laccases, peroxidases and oxidoreductases containing 2 electrons (such as uricase), where appropriate in the presence of their respective donor or cofactor.

The pH of the ready-to-use composition applied to the keratin fibers [composition resulting from the mixture of the dyeing composition A and of the oxidizing composition B], is generally between the values of 4 and 11. It is preferably between 6 and 10, and may be adjusted to the desired value by means of acidifying or alkalinizing agents well known in the state of the art for dyeing keratin fibers.

Among the alkalinizing agents, there may be mentioned by way of example aqueous ammonia, alkali metal carbonates, alkanolamines such as mono-, di- and triethanolamines as well their derivatives, oxyethylenated and/or oxypropylenated ethylenediamines and hydroxyalkylamines, sodium or potassium hydroxides and compounds having the following formula (XXVI):

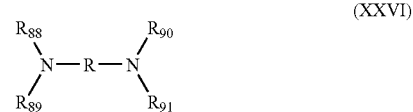

(XXVI)

in which R is a propylene residue optionally substituted with a hydroxyl group or a $C_1$–$C_4$ alkyl radical; $R_{88}$, $R_{89}$, $R_{90}$ and $R_{91}$, which are identical or different, represent a hydrogen atom, a $C_1$–$C_4$ alkyl or $C_1$–$C_4$ hydroxyalkyl radical.

The acidifying agents are conventionally, by way of example, inorganic or organic acids such as hydrochloric acid, orthophosphoric acid, carboxylic acids such as tartaric acid, citric acid, lactic acid or sulfonic acids.

The dyeing method according to the invention preferably consists in applying the ready-to-use composition, freshly prepared at the time of use from the compositions A and B described above, to the dry or wet keratin fibers, and in allowing it to act for an exposure time preferably varying from 1 to 60 minutes approximately, and more preferably from 10 to 45 minutes approximately, in rinsing the fibers, and optionally in washing them with shampoo, and then in rinsing them again, and in drying them.

A variant of this method consists in taking a composition A' comprising at least one oxidation dye but with no cationic polymer of the invention, a composition A" containing at least one cationic poly(vinyllactam) according to the invention, and in mixing, at the time of use, these compositions A' and A″ with the composition B, and then in applying and allowing the mixture obtained to act as before.

According to said methods, the compositions A, A′ and/or B may contain in addition at least one additional cationic or amphoteric polymer and at least one surfactant.

A concrete example illustrating the invention is indicated below, without however exhibiting a limiting character.

EXAMPLE

The following compositions were prepared:

(quantities expressed in grams)

| Oxidizing composition: | | |
| --- | --- | --- |
| Fatty alcohol | | 2.3 |
| Oxyethylenated fatty alcohol | | 0.6 |
| Fatty amine | | 0.9 |
| Glycerin | | 0.5 |
| Hydrogen peroxide | | 7.5 |
| Perfume | | qs |
| Demineralized water | qs | 100 |
| Dyeing composition: | | |
| Oxyethylenated fatty alcohols | | 32.5 |
| Oleic acid | | 2 |
| Oleyl alcohol | | 1.8 |
| Fatty amide | | 4 |
| Glycerin | | 3 |
| Cationic polymer of formula (W) as a 60% solution in water | | 2 |
| Amphoteric additional polymer (Merquat 280) | | 2 |
| Sequestering agent | | qs |
| Reducing agent | | qs |
| Aqueous ammonia (20% NH3) | | 8 |
| Para-phenylenediamine | | 0.324 |
| 2-Methyl-4-aminophenol | | 0.369 |
| Polymer according to the invention** | | 1.0 AS* |
| Water qs | | 100 |

AS* = Active Substance
The polymer according to the invention** is a vinylpyrrolidone/dimethylaminopropylmethacrylamide/lauryldimethylmethacrylamidoammonium chloride terpolymer provided by the company ISP under the reference POLYMER ACP-1234.

The dyeing composition was mixed, at the time of use, in a plastic bowl and for 2 minutes, with the oxidizing composition given above, in an amount of 1 part of dyeing composition per 1.5 parts of oxidizing composition.

The mixture obtained was applied to locks of natural grey hair which is 90% white and allowed to act for 30 minutes.

The locks were then rinsed with water, they were washed with standard shampoo and again rinsed with water, and then dried and disentangled.

The hair was then dyed in an intense red-purple.

The invention claimed is:

1. A composition for oxidation dyeing of keratin fibers, comprising, in an appropriate dyeing medium, at least one oxidation dye and at least one cationic poly(vinyllactam) polymer comprising:
   a) at least one monomer chosen from vinyllactam and alkylvinyllactam monomers;
   b) at least one monomer chosen from those of the following formulae (I) and (II):

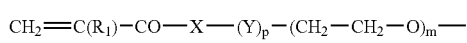
(I)

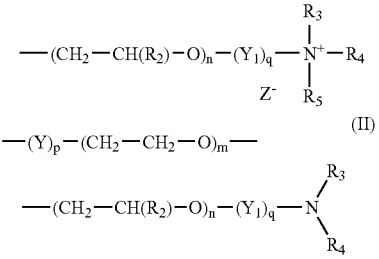
(II)

wherein:
X is chosen from an oxygen atom and $NR_6$ radicals,
$R_1$ and $R_6$, which may be identical or different, are chosen from a hydrogen atom and linear and branched $C_1$–$C_5$ alkyl radicals,
$R_2$ is chosen from linear and branched $C_1$–$C_4$ alkyl radicals,
$R_3$, $R_4$ and $R_5$, which may be identical or different, are chosen from a hydrogen atom, linear and branched $C_1$–$C_{30}$ alkyl radicals and radicals of formula (III):

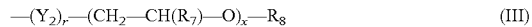
(III)

Y, $Y_1$ and $Y_2$, which may be identical or different, are chosen from linear and branched $C_2$–$C_{16}$ alkylene radicals,
$R_7$ is chosen from a hydrogen atom, linear and branched $C_1$–$C_4$ alkyl radicals, and linear and branched $C_1$–$C_4$ hydroxyalkyl radicals,
$R_8$ is chosen from a hydrogen atom and linear and branched $C_1$–$C_{30}$ alkyl radicals,
p, q and r, which may be identical or different, are each either zero or 1,
m and n, which may be identical or different, are each an integer ranging from 0 to 100,
x is an integer ranging from 1 to 100,
$Z^-$ is an anion chosen from organic and inorganic acid anions,
wherein:
at least one of the substituents $R_3$, $R_4$, $R_5$ and $R_8$ is chosen from linear and branched $C_9$–$C_{30}$ alkyl radicals,
if m or n is different from zero, then q is equal to 1, and
if m or n is equal to zero, then p or q is equal to 0.

2. The composition according to claim 1, wherein the vinyllactam and alkylvinyllactam monomers are chosen from monomers of the formula (IV):

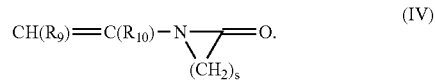
(IV)

wherein:
s is an integer ranging from 3 to 6,
$R_9$ is chosen from a hydrogen atom and $C_1$–$C_5$ alkyl radicals, and
$R_{10}$ is chosen from a hydrogen atom and $C_1$–$C_5$ alkyl radicals,
provided that at least one of the radicals $R_9$ and $R_{10}$ is a hydrogen atom.

3. The composition according to claim 2, wherein the monomers of formula (IV) comprise vinylpyrrolidone.

4. The composition according to claim 1, wherein, in formulae (I) and (II), the radicals $R_3$, $R_4$ and $R_5$, which may be identical or different, are chosen from a hydrogen atom and linear and branched $C_1$–$C_{30}$ alkyl radicals.

5. The composition according to claim 1, wherein the at least one monomer b) is chosen from the monomers of formula (I).

6. The composition according to claim 5, wherein, in formula (I), m and n are equal to zero.

7. The composition according to claim 1, wherein the counterion $Z^-$ of the monomers of formula (I) is chosen from halide ions, phosphate ions, a methosulfate ion and a tosylate ion.

8. The composition according to claim 1, wherein the at least one cationic poly(vinyllactam) polymer comprises at least one additional monomer chosen from cationic and nonionic monomers.

9. The composition according to claim 8, wherein the at least one cationic poly(vinyllactam) polymer is chosen from terpolymers comprising:

(a) one monomer of formula (IV), (b) one monomer of formula (I), wherein: p=1, q=0, $R_3$ and $R_4$, which may be identical or different, are chosen from a hydrogen atom and $C_1$–$C_5$ alkyl radicals, and $R_5$ is chosen from $C_9$–$C_{24}$ alkyl radicals, and (c) one monomer of formula (II), wherein: $R_3$ and $R_4$, which may be identical or different, are chosen from a hydrogen atom and $C_1$–$C_5$ alkyl radicals.

10. The composition according to claim 9, wherein the terpolymers comprise, by weight, from 40% to 95% of the monomer (a), from 0.25% to 50% of the monomer (b) and from 0.1% to 55% of the monomer (c).

11. The composition according to claim 1, wherein the at least one cationic poly(vinyllactam) polymer is chosen from terpolymers vinylpyrrolidone/dimethylaminopropylmethacrylamide/dodecyldimethylmethacrylamidopropylammonium tosylate, terpolymers vinylpyrrolidone/dimethylaminopropylmethacrylamide/cocoyidimethylmethacrylamidopropylammonium tosylate, terpolymers vinylpyrrolidone/dimethylaminopropylmethacrylamide/lauryldimethylmethacrylamidopropylammonium tosylate and chloride.

12. The composition according to claim 1, wherein the weight-average molecular mass of the at least one cationic poly(vinyllactam) polymer ranges from 500 to 20 000 000.

13. The composition according to claim 1, wherein the at least one cationic poly(vinyllactam) polymer is in an amount ranging from 0.01 to 10% by weight of the total weight of the composition.

14. The composition according to claim 13, wherein the at least one cationic poly(vinyllactam) polymer is in an amount ranging from 0.1% to 5% by weight of the total weight of the composition.

15. The composition according to claim 1, wherein the at least one oxidation dye is chosen from oxidation bases and couplers.

16. The composition according to claim 15, wherein the oxidation bases are chosen from ortho- and para-phenylenediamines, double bases, ortho- and para-aminophenols, and heterocyclic bases, and the acid addition salts thereof.

17. The composition according to claim 16, wherein the para-phenylenediamines are chosen from the compounds of the following formula (V):

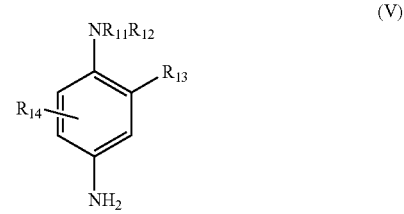

wherein:
$R_{11}$ is chosen from a hydrogen atom, $C_1$–$C_4$ alkyl radicals, monohydroxy($C_1$–$C_4$ alkyl) radicals, polyhydroxy ($C_2$–$C_4$ alkyl) radicals, ($C_1$–$C_4$)alkoxy($C_1$–$C_4$)alkyl radicals, $C_1$–$C_4$ alkyl radicals substituted with at least one nitrogen-containing group, a phenyl radical, and a 4'-aminophenyl radical;

$R_{12}$ is chosen from a hydrogen atom, $C_1$–$C_4$ alkyl radicals, monohydroxy($C_1$–$C_4$ alkyl) radicals, polyhydroxy ($C_2$–$C_4$ alkyl) radicals, ($C_1$–$C_4$)alkoxy($C_1$–$C_4$)alkyl radicals, and $C_1$–$C_4$ alkyl radicals substituted with at least one nitrogen-containing group;

$R_{11}$ and $R_{12}$ may also form with the nitrogen atom carrying them a nitrogen-containing heterocycle chosen from 5- and 6-membered nitrogen-containing heterocycles optionally substituted with at least one group chosen from alkyl, hydroxyl and ureido groups;

$R_{13}$ is chosen from a hydrogen atom, halogen atoms, $C_1$–$C_4$ alkyl radicals, a sulfo radical, a carboxyl radical, monohydroxy($C_1$–$C_4$ alkyl) radicals, hydroxy($C_1$–$C_4$ alkoxy) radicals, acetylamino($C_1$–$C_4$ alkoxy) radicals, mesylamino($C_1$–$C_4$ alkoxy) radicals, and carbamoylamino($C_1$–$C_4$ alkoxy) radicals, and $R_{14}$ is chosen from a hydrogen atom, halogen atoms, and $C_1$–$C_4$ alkyl radicals.

18. The composition according to claim 16, wherein the double bases are chosen from the compounds of the following formula (VI):

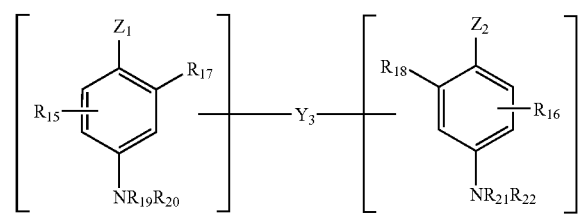

wherein:
$Z_1$ and $Z_2$, which may be identical or different, are chosen from hydroxyl and —$NH_2$ radicals which may be substituted with at least one entity chosen from $C_1$–$C_4$ alkyl radicals and a linking arm $Y_3$;

the linking arm $Y_3$ comprising an alkylene chain chosen from linear and branched alkylene chains comprising from 1 to 14 carbon atoms, which may be interrupted by or which may end with at least one entity chosen from nitrogen-containing groups and heteroatoms, and optionally substituted with at least one radical chosen from hydroxyl and $C_1$–$C_6$ alkoxy radicals;

$R_{15}$ and $R_{16}$, which may be identical or different, are chosen from hydrogen and halogen atoms, $C_1$–$C_4$ alkyl radicals, monohydroxy($C_1$–$C_4$ alkyl) radicals, polyhydroxy($C_2$–$C_4$ alkyl) radicals, amino($C_1$–$C_4$ alkyl) radicals, and the linking arm $Y_3$; and $R_{17}$, $R_{18}$, $R_{19}$, $R_{20}$, $R_{21}$ and $R_{22}$, which may be identical or different, are chosen from a hydrogen atom, the linking arm $Y_3$, and $C_1$–$C_4$ alkyl radicals;

wherein the compounds of formula (VI) contain only one linking arm $Y_3$ per molecule.

19. The composition according to claim 18, wherein the heteroatoms of the linking arm $Y_3$ are chosen from oxygen, sulfur, and nitrogen atoms.

20. The composition according to claim 16, wherein the para-aminophenols are chosen from the compounds of the following formula (VII):

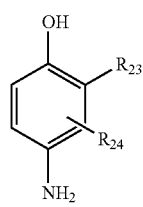

(VII)

wherein:
$R_{23}$ is chosen from a hydrogen atom, halogen atoms, and $C_1$–$C_4$ alkyl, monohydroxy($C_1$–$C_4$ alkyl), ($C_1$–$C_4$) alkoxy($C_1$–$C_4$)alkyl, amino($C_1$–$C_4$ alkyl), and hydroxy ($C_1$–$C_4$)alkylamino($C_1$–$C_4$ alkyl) radicals, and $R_{24}$ is chosen from a hydrogen atom, halogen atoms, and $C_1$–$C_4$ alkyl, monohydroxy($C_1$–$C_4$ alkyl), polyhydroxy ($C_2$–$C_4$ alkyl), amino($C_1$–$C_4$ alkyl), cyano($C_1$–$C_4$ alkyl), and ($C_1$–$C_4$)alkoxy($C_1$–$C_4$)alkyl radicals.

21. The composition according to claim 16, wherein the heterocyclic bases are chosen from pyridine derivatives, pyrimidine derivatives, and pyrazole derivatives.

22. The composition according to claim 21, wherein the pyrimidine derivatives are chosen from pyrazolopyrimidines.

23. The composition according to claim 15, wherein the oxidation bases are in an amount ranging from 0.0005% to 12% by weight relative to the total weight of the composition.

24. The composition according to claim 15, wherein the couplers are chosen from meta-phenylenediamines, meta-aminophenols, meta-diphenols, heterocyclic couplers, and the acid addition salts thereof.

25. The composition according to claim 15, wherein the couplers are in an amount ranging from 0.0001% to 10% by weight relative to the total weight of the composition.

26. The composition according to claim 16, wherein the acid addition salts are chosen from hydrochlorides, hydrobromides, sulfates, tartrates, lactates, and acetates.

27. The composition according to claim 24, wherein the acid addition salts are chosen from hydrochlorides, hydrobromides, sulfates, tartrates, lactates, and acetates.

28. The composition according to claim 1, further comprising at least one direct dye.

29. The composition according to claim 28, wherein the at least one direct dye is chosen from neutral, cationic, and anionic nitro, azo and anthraquinone dyes.

30. The composition according to claim 28, wherein the at least one direct dye is in an amount ranging from 0.001% to 20% by weight relative to the total weight of the composition.

31. The composition according to claim 1, further comprising at least one additional polymer chosen from amphoteric polymers and cationic polymers different from the at least one cationic poly(vinyllactam) polymer.

32. The composition according to claim 31, wherein the cationic polymers different from the at least one cationic poly(vinyllactam) polymer are chosen from quaternary polyammoniums comprising repeating units corresponding to the following formula (W):

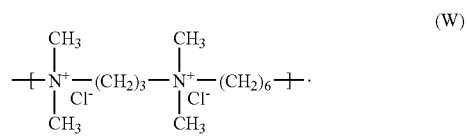

(W)

33. The composition according to claim 31, wherein the cationic polymers different from the at least one cationic poly(vinyllactam) polymer are chosen from quaternary polyammoniums comprising repeating units corresponding to the following formula (U):

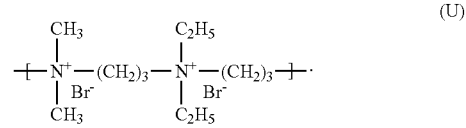

(U)

34. The composition according to claim 31, wherein the amphoteric polymers are chosen from copolymers comprising at least, as monomers, an acrylic acid and a salt of dimethyldiallylammonium.

35. The composition according to claim 31, wherein the at least one additional polymer is in an amount ranging from 0.01% to 10% by weight relative to the total weight of the composition.

36. The composition according to claim 1, further comprising at least one surfactant chosen from anionic, cationic, nonionic, and amphoteric surfactants.

37. The composition according to claim 36, wherein the at least one surfactant is in an amount ranging from 0.01% to 40% by weight relative to the total weight of the composition.

38. The composition according to claim 1, further comprising at least one additional thickening agent.

39. The composition according to claim 38, wherein the at least one additional thickening agent is chosen from cellulose derivatives, guar derivatives, gums of microbial origin, and synthetic thickeners.

40. The composition according to claim 38, wherein the at least one additional thickening agent is in an amount ranging from 0.01% to 10% by weight relative to the total weight of the composition.

41. The composition according to claim 1, further comprising at least one reducing agent.

42. The composition according to claim 41, wherein the at least one reducing agent is in an amount ranging from 0.05% to 3% by weight relative to the total weight of the composition.

43. The composition according to claim 1, further comprising at least one oxidizing agent.

44. The composition according to claim 43, wherein the at least one oxidizing agent is chosen from hydrogen peroxide, urea peroxide, alkali metal bromates and ferricyanides, persalts, and oxidation-reduction enzymes with optionally their respective donor or cofactor.

45. A method for dyeing keratin fibers, comprising applying to the keratin fibers at least one composition (A) comprising, in an appropriate dyeing medium, at least one oxidation dye, wherein color is developed at alkaline, neutral or acidic pH with the aid of a composition (B) comprising at least one oxidizing agent, which is mixed at the time of use with the composition (A) or which is applied sequentially without intermediate rinsing, wherein at least one of the composition (A) and the composition (B) further comprises at least one cationic poly(vinyllactam) polymer comprising:
 a) at least one monomer chosen from vinyllactam and alkylvinyllactam monomers;
 b) at least one monomer chosen from those of the following formulae (I) and (II):

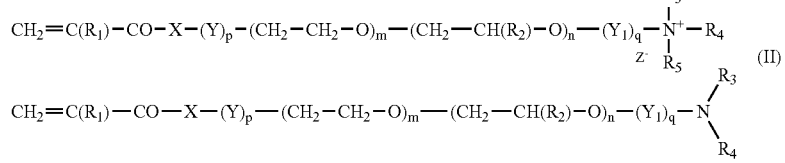

wherein:
X is chosen from an oxygen atom and radicals $NR_6$,
$R_1$ and $R_6$, which may be identical or different, are chosen from a hydrogen atom and linear and branched $C_1$–$C_5$ alkyl radicals,
$R_2$ is chosen from linear and branched $C_1$–$C_4$ alkyl radicals,
$R_3$, $R_4$ and $R_5$, which may be identical or different, are chosen from a hydrogen atom, linear and branched $C_1$–$C_{30}$ alkyl radicals and radicals of formula (III):

$$-(Y_2)_r-(CH_2-CH(R_7)-O)_x-R_8 \quad (III)$$

Y, $Y_1$ and $Y_2$, which may be identical or different, are chosen from linear and branched $C_2$–$C_{16}$ alkylene radicals,
$R_7$ is chosen from a hydrogen atom, linear and branched $C_1$–$C_4$ alkyl radicals, and linear and branched $C_1$–$C_4$ hydroxyalkyl radicals, $R_8$ is chosen from a hydrogen atom and linear and branched $C_1$–$C_{30}$ alkyl radicals,
p, q and r, which may be identical or different, are each either zero or 1,
m and n, which may be identical or different, are each an integer ranging from 0 to 100,
x is an integer ranging from 1 to 100,
$Z^-$ is an anion chosen from organic and inorganic acid anions, wherein:
 at least one of the substituents $R_3$, $R_4$, $R_5$ and $R_8$ is chosen from linear and branched $C_9$–$C_{30}$ alkyl radicals,
 if m or n is different from zero, then q is equal to 1, and
 if m or n is equal to zero, then p or q is equal to 0.

46. The method according to 45, comprising applying to dry or wet keratin fibers said composition, allowing the composition to act for an exposure time ranging from 1 to 60 minutes, rinsing the keratin fibers, and then optionally washing the keratin fibers with shampoo, rinsing the keratin fibers again, and drying the keratin fibers,
 wherein the composition is prepared at the time of use by combining the composition (A) with the composition (B).

47. A method for dyeing keratin fibers, comprising applying to dry or wet keratin fibers a ready-to-use composition, allowing the composition to act for an exposure time ranging from 1 to 60 minutes, rinsing the keratin fibers, and then optionally washing the keratin fibers with shampoo, rinsing the keratin fibers again, and drying the keratin fibers,
 wherein the ready-to-use composition is prepared at the time use by combining a composition A' comprising, in an appropriate dyeing medium, at least one oxidation dye; a composition A" comprising, in an appropriate dyeing medium, at least one cationic poly(vinyllactam) polymer comprising:

a) at least one monomer chosen from vinyllactam and alkylvinyllactam monomers;

b) at least one monomer chosen from those of the following formulae (I) and (II):

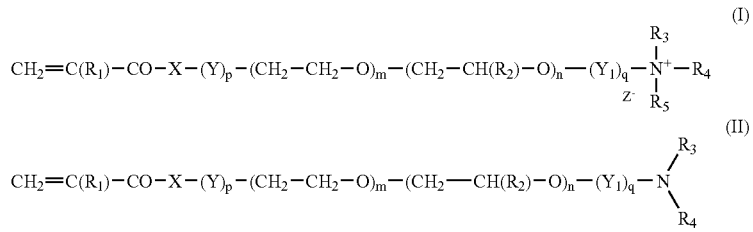

wherein:
X is chosen from an oxygen atom and $NR_6$ radicals,
$R_1$ and $R_6$, which may be identical or different, are chosen from a hydrogen atom and linear and branched $C_1$–$C_5$ alkyl radicals,
$R_2$ is chosen from linear and branched $C_1$–$C_4$ alkyl radicals,
$R_3$, $R_4$ and $R_5$, which may be identical or different, are chosen from a hydrogen atom, linear and branched $C_1$–$C_{30}$ alkyl radicals and radicals of formula (III):

$$(Y_2)_r-(CH_2-CH(R_7)-O)_x-R_8 \quad (III)$$

Y, $Y_1$ and $Y_2$, which may be identical or different, are chosen from linear and branched $C_2$–$C_{16}$ alkylene radicals, $R_7$ is chosen from a hydrogen atom, linear and branched $C_1$–$C_4$ alkyl radicals, and linear and branched $C_1$–$C_4$ hydroxyalkyl radicals, $R_8$ is chosen from a hydrogen atom and linear and branched $C_1$–$C_{30}$ alkyl radicals, p, q and r, which may be identical or different, are each either zero or 1, m and n, which may be identical or different, are each an integer ranging from 0 to 100, x is an integer ranging from 1 to 100, $Z^-$ is an anion chosen from organic and inorganic acid anions, wherein:

at least one of the substituents $R_3$, $R_4$, $R_5$ and $R_8$ is chosen from linear and branched $C_9$–$C_{30}$ alkyl radicals, if m or n is different from zero, then q is equal to 1, and if m or n is equal to zero, then p or q is equal to 0; and an oxidizing composition B comprising, in an appropriate dyeing medium, at least one oxidizing agent, wherein the composition A' does not comprise the at least one cationic poly(vinyllactam) polymer.

48. The method according to claim 45, wherein at least one of the composition A and the composition B further comprises at least one surfactant and at least one additional polymer chosen from amphoteric polymers and cationic polymers different from the at least one cationic poly(vinyllactam) polymer.

49. The method according to claim 47, wherein at least one of the composition A' and the composition B further comprises at least one surfactant and at least one additional polymer chosen from amphoteric polymers and cationic polymers different from the at least one cationic poly(vinyllactam) polymer.

50. A multi-compartment device for dyeing keratin fibers, comprising a first compartment comprising a composition A1 comprising, in an appropriate dyeing medium, at least one oxidation dye, and a second compartment comprising a composition B1 comprising, in an appropriate dyeing medium, at least one oxidizing agent, wherein at least one of the composition A1 and the composition B1 comprises at least one cationic poly(vinyllactam) polymer comprising a) at least one monomer chosen from vinyllactam and alkylvinyllactam monomers;

b) at least one monomer chosen from those of the following formulae (I) and (II):

wherein:

X is chosen from an oxygen atom and $NR_6$ radicals, $R_1$ and $R_6$, which may be identical or different, are chosen from a hydrogen atom and linear and branched $C_1$–$C_5$ alkyl radicals, $R_2$ is chosen from linear and branched $C_1$–$C_4$ alkyl radicals, $R_3$, $R_4$ and $R_5$, which may be identical or different, are chosen from a hydrogen atom, linear and branched $C_1$–$C_{30}$ alkyl radicals and radicals of formula (III):

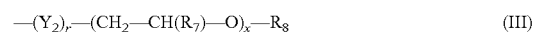

Y, $Y_1$ and $Y_2$, which may be identical or different, are each chosen from linear and branched $C_2$–$C_{16}$ alkylene radicals, $R_7$ is chosen from a hydrogen atom, linear and branched $C_1$–$C_4$ alkyl radicals, and linear and branched $C_1$–$C_4$ hydroxyalkyl radicals, $R_8$ is chosen from a hydrogen atom and linear and branched $C_1$–$C_{30}$ alkyl radicals, p, q and r, which may be identical or different, are each either zero or 1, m and n, which may be identical or different, are each an integer ranging from 0 to 100, x is an integer ranging from 1 to 100, $Z^-$ is an anion chosen from organic and inorganic acid anions, wherein:

at least one of the substituents $R_3$, $R_4$, $R_5$ and $R_8$ is chosen from linear and branched $C_9$–$C_{30}$ alkyl radicals, if m or n is different from zero, then q is equal to 1, and if m or n is equal to zero, then p or q is equal to 0.

51. A multi-compartment device for dyeing keratin fibers, comprising a first compartment comprising a composition A2 comprising, in an appropriate dyeing medium, at least one oxidation dye, a second compartment comprising a composition B2 comprising, in an appropriate dyeing medium, at least one oxidizing agent, and a third compartment comprising a composition C comprising, in an appropriate dyeing medium, at least one cationic poly(vinyllactam) polymer comprising a) at least one monomer chosen from vinyllactam and alkylvinyllactam monomers;

b) at least one monomer chosen from those of the following formulae (I) and (II):

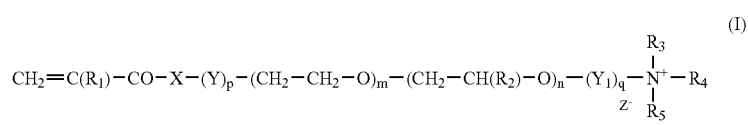

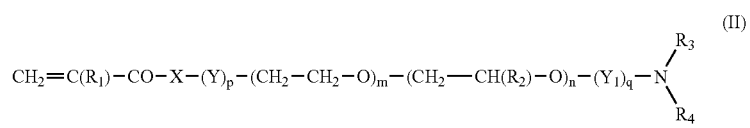

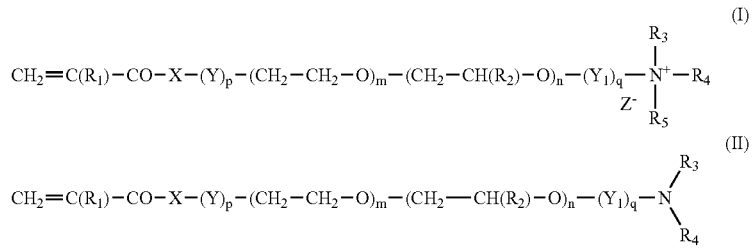

$$CH_2=C(R_1)-CO-X-(Y)_p-(CH_2-CH_2-O)_m-(CH_2-CH(R_2)-O)_n-(Y_1)_q-\overset{R_3}{\underset{R_5}{\overset{|}{N^+}}}-R_4 \quad Z^- \quad (I)$$

$$CH_2=C(R_1)-CO-X-(Y)_p-(CH_2-CH_2-O)_m-(CH_2-CH(R_2)-O)_n-(Y_1)_q-N\overset{R_3}{\underset{R_4}{\diagdown}} \quad (II)$$

wherein:

X is chosen from an oxygen atom and $NR_6$ radicals, $R_1$ and $R_6$, which may be identical or different, are chosen from a hydrogen atom and linear and branched $C_1$–$C_5$ alkyl radicals, $R_2$ is chosen from linear and branched $C_1$–$C_4$ alkyl radicals, $R_3$, $R_4$ and $R_5$, which may be identical or different, are chosen from a hydrogen atom, linear and branched $C_1$–$C_{30}$ alkyl radicals and radicals of formula (III):

$$-(Y_2)_r-(CH_2-CH(R_7)-O)_x-R_8 \quad (III)$$

Y, $Y_1$ and $Y_2$, which may be identical or different, are each chosen from linear and branched $C_2$–$C_{16}$ alkylene radicals, $R_7$ is chosen from a hydrogen atom, linear and branched $C_1$–$C_4$ alkyl radicals, and linear and branched $C_1$–$C_4$ hydroxyalkyl radicals, $R_8$ is chosen from a hydrogen atom and linear and branched $C_1$–$C_{30}$ alkyl radicals, p, q and r, which may be identical or different, are each either zero or 1, m and n, which may be identical or different, are each an integer ranging from 0 to 100, x is an integer ranging from 1 to 100, $Z^-$ is an anion chosen from organic and inorganic acid anions, wherein:

at least one of the substituents $R_3$, $R_4$, $R_5$ and $R_8$ is chosen from linear and branched $C_9$–$C_{30}$ alkyl radicals, if m or n is different from zero, then q is equal to 1, and if m or n is equal to zero, then p or q is equal to 0, wherein at least one of the composition A2 and the composition B2 may further comprise said at least one cationic poly(vinyllactam) polymer.

* * * * *